(12) United States Patent
Suess et al.

(10) Patent No.: US 6,490,336 B1
(45) Date of Patent: Dec. 3, 2002

(54) PHANTOM FOR MEASURING SLICE THICKNESSES, SLICE SENSITIVITY PROFILES AND THE AXIAL MODULATION TRANSFER FUNCTION IN AN X-RAY COMPUTED TOMOGRAPHY APPARATUS

(75) Inventors: Christoph Suess, Erlangen (DE); Willi Kalender, Moehrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/831,543
(22) PCT Filed: Nov. 10, 1999
(86) PCT No.: PCT/DE99/03576
§ 371 (c)(1),
(2), (4) Date: Jul. 23, 2001
(87) PCT Pub. No.: WO00/28898
PCT Pub. Date: May 25, 2000

(30) Foreign Application Priority Data

Nov. 12, 1998 (DE) .......................................... 198 52 324

(51) Int. Cl.$^7$ ................................................. A61B 6/00
(52) U.S. Cl. ....................... 378/18; 378/207; 250/252.1
(58) Field of Search ............................ 378/18, 4, 207, 378/19; 250/252.1

(56) References Cited

U.S. PATENT DOCUMENTS

| | | | |
|---|---|---|---|
| 4,972,451 A | 11/1990 | Brok et al. | |
| 5,164,978 A | 11/1992 | Goodenough et al. | |
| 5,416,816 A | * 5/1995 | Wenstrup et al. | 378/18 |
| 5,506,884 A | * 4/1996 | Goodenough et al. | 250/252.1 |
| 5,561,698 A | 10/1996 | Mick et al. | |
| 5,793,835 A | * 8/1998 | Blanck | 378/18 |

OTHER PUBLICATIONS

"Physical Performance Characteristics of Spiral CT Scanning," Kalender et al., Med. Phys. vol. 18, No. 5, Sep./Oct. 1991, pp. 910–915.
"Performance Evaluation and Quality Control in Spiral CT," Seuss et al., Medical CT and & Ultrasound: Current Technology and Applications, Goldman et al., Eds. (1995), pp. 467–485.
A Comparison of Conventional and Spiral CT: An Experimental Study on the Detection of Spherical Lesions, Kalender et al., J. of Comp. Assisted Tomography, vol. 18, No. 2, Mar./Apr. 1994, pp. 167–176.
Determination of Spiral CT Slice Sensitivity Profiles Using a Point Response Phantom, Davros et al., J. of Comp. Assisted Tomography, vol. 19, No. 5, Sep./Oct. 1995, pp. 838–843.

* cited by examiner

Primary Examiner—David V. Bruce
Assistant Examiner—Pamela R. Hobden
(74) Attorney, Agent, or Firm—Schiff Hardin & Waite

(57) ABSTRACT

A phantom for measuring slice thicknesses, slice sensitivity profiles and the axial modulation transfer function in an X-ray computed tomography apparatus contains a foil of a material that highly attenuates X-radiation that is arranged parallel to the image plane of the X-ray computed tomography apparatus given employment of the phantom and which had an axial expanse that is small compared to the thinnest slice to be measured. The expanse of the foil in the direction of the image plane is on the order of magnitude of a few millimeters.

17 Claims, 4 Drawing Sheets

PHANTOM FOR MEASURING SLICE THICKNESSES, SLICE SENSITIVITY PROFILES AND THE AXIAL MODULATION TRANSFER FUNCTION IN AN X-RAY COMPUTED TOMOGRAPHY APPARATUS

BACKGROUND OF THE INVENTION

1. Field of the Invention

The present invention is directed to a phantom for measuring slice thicknesses, slice sensitivity profiles and the axial modulation transfer function (MTF) in an X-ray computed tomography apparatus.

2. Description of the Prior Art

In X-ray computer tomography (CT), the measurement field is limited in the axial direction by intense gating of the useful x-ray beam and a slice having an allocated thickness, referred to as the slice thickness, is thus defined. For numerous reasons, this measurement field gating is experimentally identified or checked with suitable measurement means. The measurement means employed which have been conventionally employed allow the measurement of the slice sensitivity profile in a spiral CT exposure and an exact acquisition of extremely thin slices (1 mm and less) in a single-slice exposure inadequately or not at all.

In conformity with standards, the slice profiles in CT are measured with phantoms known as ramp phantoms (for example, DIN 6868, Part 53). These are thin, highly attenuating objects lying obliquely in the examination slice, usually metal wires or strips. This is well-suited for single-slice exposures having standard slice thickness of 2 mm and more. For thinner slices, relatively high systematic errors occur due to the finite thickness of the metals. These test bodies are not suited at all for volume exposure with spiral CT since they produce pronounced image errors (see Ch. S üβ, W. A. Kalender, "Performance Evaluation and Quality Control in Spiral CT", in *Medical CT and Ultrasound: Current Technology and Applications*, pp. 467–485, American Association of Physicists in Medicine/Advanced Medical Publishing, 1995).

Attempts have been made for several years to find a suitable measurement phantom. In 1994, thus, W. A. Kalender et al., "A Comparison of Conventional and Spiral CT: An Experimental Study on the Detection of Spherical Lesions", in *Journal of Computer Assisted Tomography*, 18(2): 167–176, March/April, 1994, Ravel Press Ltd., New York, describes the measurement of the axial image [sic] function (MTF), i.e. of the slice profile, with minute lead balls.

Small copper or steel balls were employed in 1995 by Davros et al., "Determination of Spiral CT Slice Sensitivity Profiles Using a Point Response Phantom", in *Journal of Computer Assisted Tomography*, 19(5):838–843, September/October, 1995, Lippincoft-Raven Publishers, Philadelphia. Such a phantom has been offered in the meantime by 'Nuclear Associates, USA'.

A similar phantom was disclosed in 1992 in U.S. Pat. No. 5,164,978 for measuring the MTF in the image plane; however, it could also be employed for measuring the axial MTF.

Fundamentally, these ball phantoms are very well-suited for the measurement but have the disadvantage that the subject contrast is extremely low: the expanse dare not amount to more than 1/10 of the slice thickness, so that the contrast already drops to below 10% due to the partial volume effect. As a result of the MTF in the image plane, the contrast drops again to about 1%, i.e. drops overall to approximately 0.1% of the original value and thus deteriorates the measurement precision of the method. Different ball diameters are therefore employed dependent on the slice thickness. Moreover, the manufacture of minutes balls (100 through 500 $\mu$m) is not simple to realize technologically. For example, the test phantom of 'Nuclear Associates' contains a piece of copper wire that inadequately simulates the spherical shape and therefore produces pronounced measurement errors.

DIN 6866, Part 10, proposes a phantom based on a plastic body with a shallow cavity. The contrast between air and plastic, however, is relatively low. The cavity must therefore have a large diameter, which in turns makes the exact positioning parallel to the image plane more difficult. Similar problems occur in the phantom of the type initially described, as reported by W. A. Kalender et al. Polacin [sic], "Physical performance characteristics of spiral CT scanning", in Med. Phys. 18(5):910–915, September/Octobetr 1991, am. Assoc. Phys. Med., 1995, whereby an aluminum foil having a diameter of 16 cm is placed between two plastic disks having the same diameter. Difficulties in the alignment can also occur given a phantom of the type initially described that is known from U.S. Pat. No. 5,793,835.

In conjunction with the measurement of slice sensitivity profiles and axial modulation transfer functions, the aforementioned U.S. Pat. No. 5,164,978 as well as U.S. Pat. No. 4,972,451 disclose that the expanse of the structures utilized in phantoms for this calibration should be smaller than the smallest or thinnest structure to be measured. U.S. Pat. No. 5,164,978 also discloses the employment in this context of material that highly attenuates X-radiation. This employment is also known from U.S. Pat. No. 5,561,698.

SUMMARY OF THE INVENTION

An object of the present invention is to provide a phantom of the type initially described which provides adequate subject contrast but wherein the dimension in the slice plane is nonetheless slight.

This object is inventively achieved by a phantom for measuring slice thicknesses, slice sensitivity profiles and the axial modulation transfer function in an X-ray computed tomography apparatus that contains a foil composed of a material that is highly attenuating for X-radiation, that is arranged parallel to the image plane of the X-ray computer tomograph given employment of the phantom, and which has an axial expanse that is small compared to the thinnest slice to be measured and which has an expanse in the direction of the image plane of the X-ray computed tomography apparatus that is on the order of magnitude of a few millimeters. By employing a foil of a material that is highly attenuating for X-radiation—materials whose atomic number amounts to at least 13 are especially suitable—, a significantly higher subject contrast is achieved compared to small balls of aluminum, iron or copper or[, respectively,] compared to an air gap, even though the foil can be very thin. For standard X-ray computer tomography systems, the thickness of the foil is then small compared to the axial expanse of the thinnest slice to be measured when the thickness of the foil amounts to between 10 and 100 $\mu$m. Since the expanse of the foil in the direction of the image plane of the X-ray computer tomography apparatus lies on the order of magnitude of a few millimeters, the alignment of the foil parallel to the image plane can be easily accomplished. Second, the small expanse of the foil in the direction of the image plane of the X-ray computed tomography apparatus prevents a lowering of the subject contrast due to the MTF of the X-ray computed tomography apparatus.

Compared to small balls, moreover, foils offer the advantage that they are technologically easy to manufacture and process.

In the interests of an easy manipulation of the phantom, in one version of the invention the foil is accepted in a homogeneous material; homogeneous plastics are particularly suitable, as is a water container.

The inventive phantom thus combines the advantages of small metal balls, namely slight expanse perpendicular to the image plane of the X-ray computed tomography apparatus and high X-ray attenuation, with the advantages of an air gap, namely ease of manufacture and low reduction of the subject contrast due to the MTF of the X-ray computer tomography apparatus. The invention allows all slice thicknesses that are currently standard to be measured with a single phantom since the obtainable subject contrast suffices not only for slice thicknesses in the sub-millimeter range but also for thicker slices.

DESCRIPTION OF THE PREFERRED EMBODIMENTS

Figure 1:
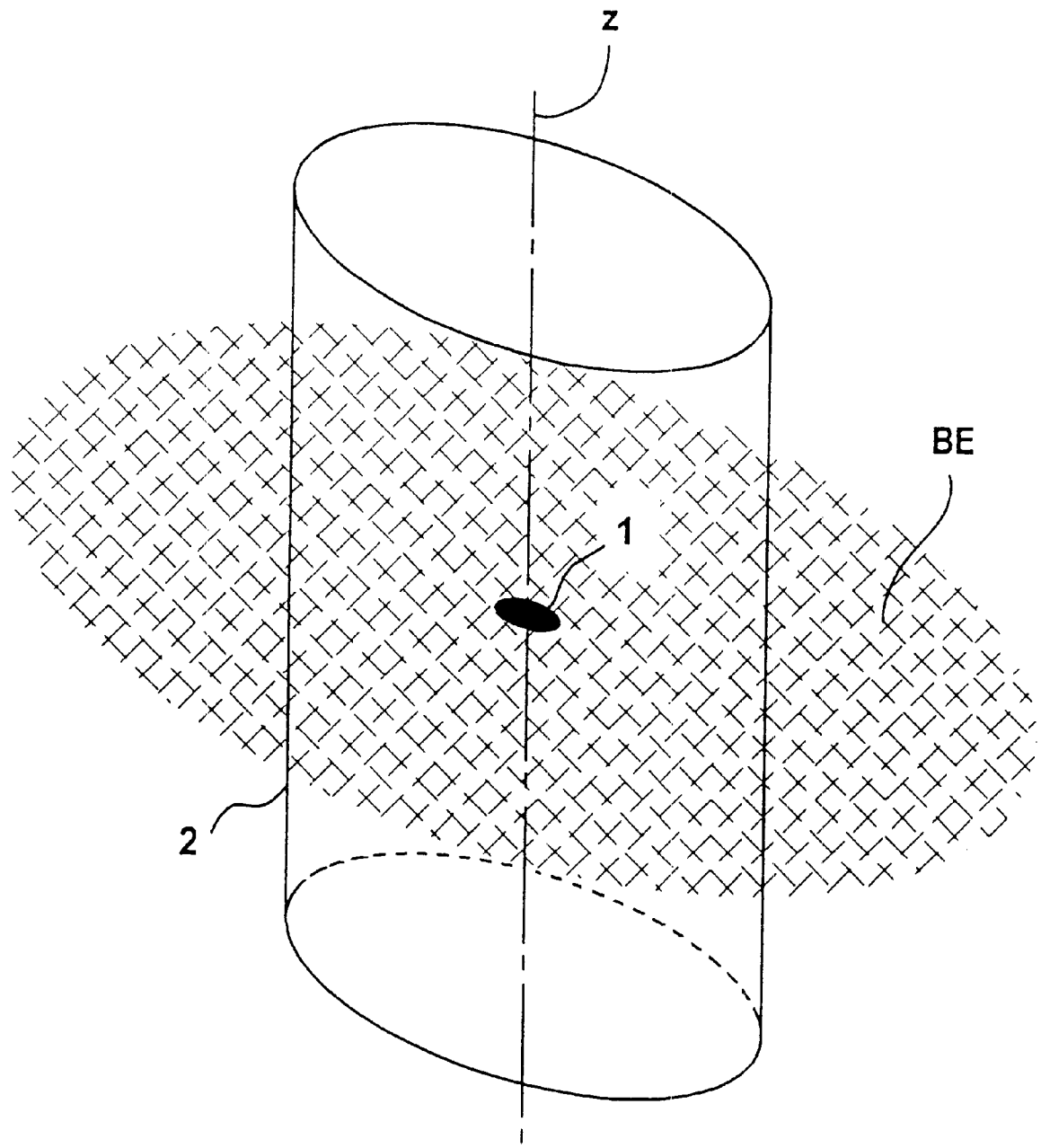
FIGS. 1 and 2 show inventive phantoms in a perspective views.

As shown in FIG. 1, the inventive phantom has a foil 1 of material that highly attenuates X-radiation, i.e. a material having an atomic number of at least 13, that, for example, is composed of lead, tantalum or gold, as in the exemplary embodiment. The foil 1 has a thickness between 10 and 100 $\mu$m, 50 $\mu$m in the case of the exemplary embodiment. In order to avoid artifacts when used in a spiral computed tomography apparatus, the foil 1 has a circular contour, [whereby] the diameter of the foil 1 being on the order of magnitude of a few millimeters, for example 1 through 5 mm, and is 2 mm in the exemplary embodiment. The foil is embedded in a cylindrical, rod-shaped member 2 composed of a homogeneous plastic, polyurethane in the exemplary embodiment, such that the foil 1 lies in the image plane BE (indicated as a dotted surface in FIG. 1) during operation of the phantom. The image plane BE in turn is perpendicular to the system and rotational axis (referenced z) of an X-ray computed tomography apparatus.

For reducing the image noise, the diameter of the member 2 is to only a few cm; dependent on the requirements, the length can, for example, amount to up to 10 cm.

Figure 2:
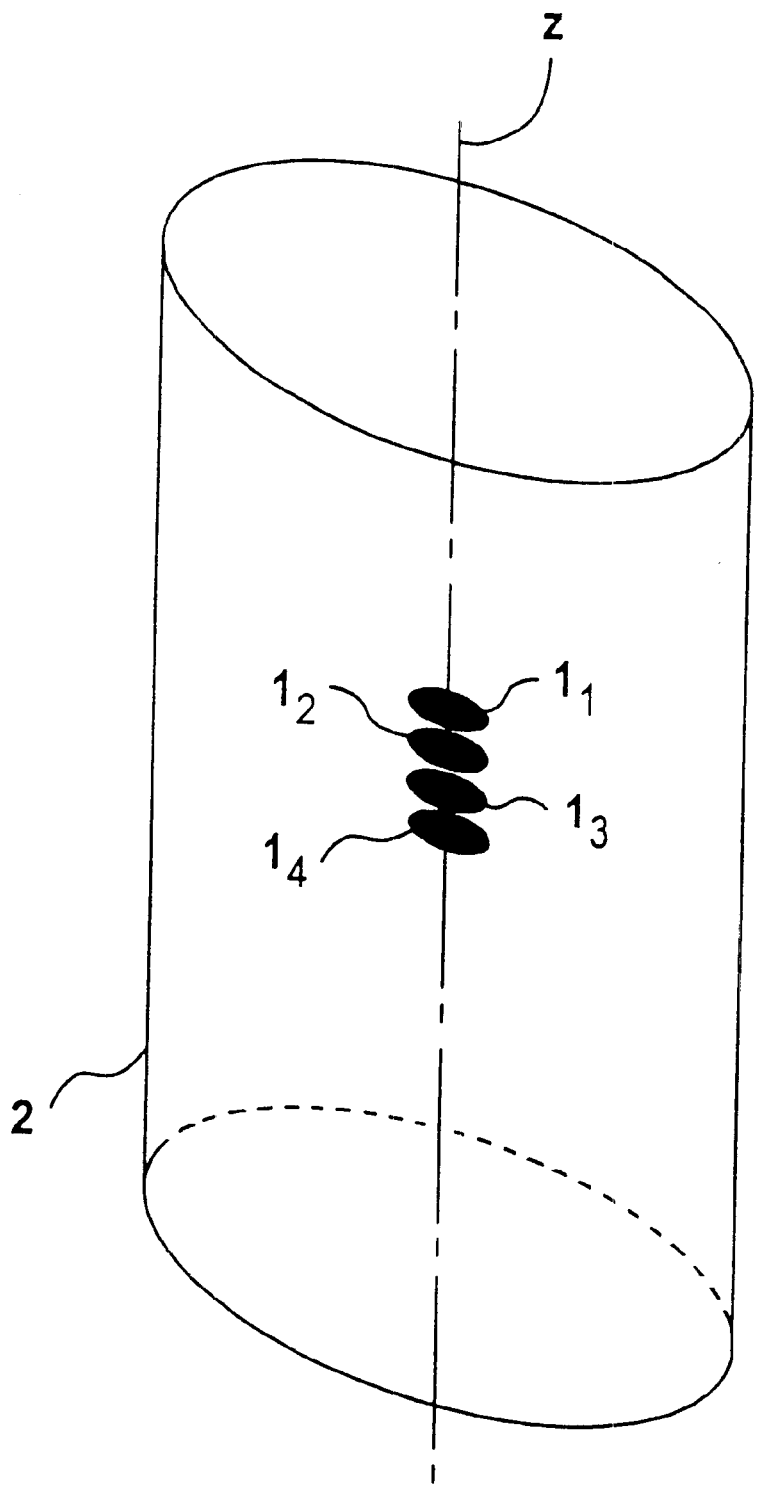

FIG. 2 shows a further inventive phantom that is provided for employment in X-ray computed systems with multi-line detectors, and therefore the phantom has a number of foils $1_1$ through $1_4$ arranged successively in the direction of the z-axis. Otherwise, the phantom shown in FIG. 2 corresponds to the phantom according to FIG. 1.

Figure 3:
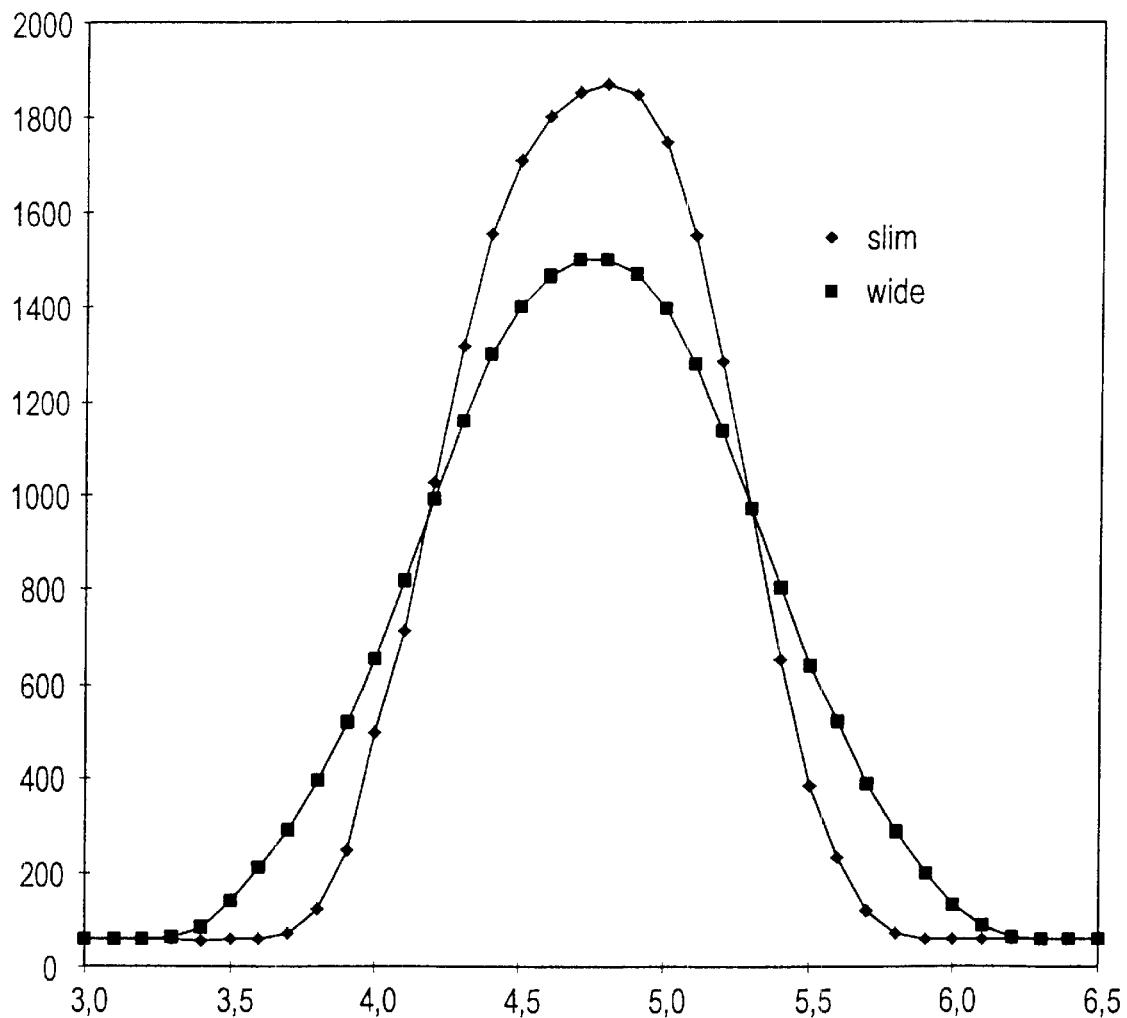
FIGS. 3 and 4 show measured results achieved with the phantom according to FIG. 1.
Figure 4:
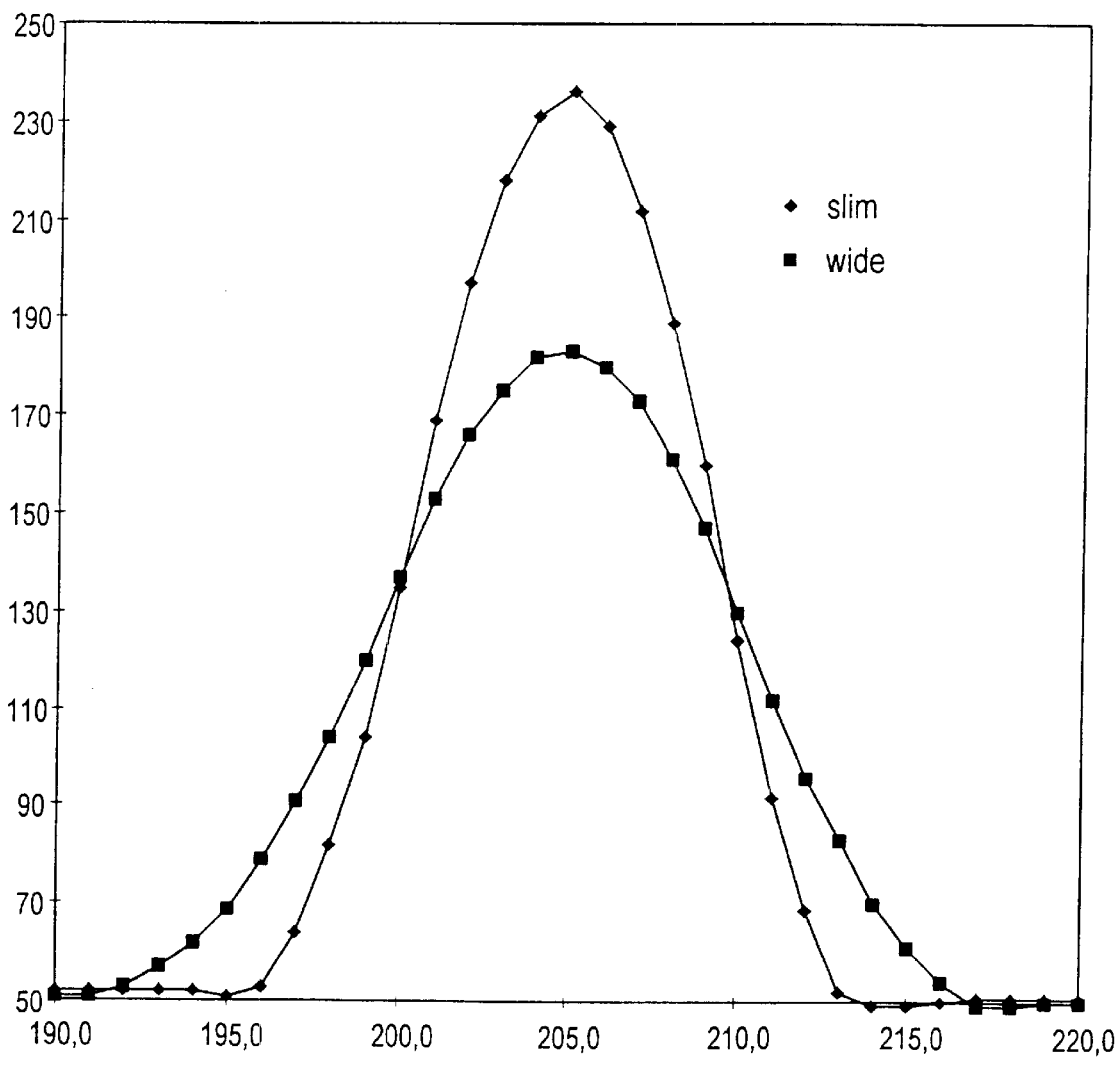

FIGS. 3 and 4 show slice sensitivity profiles measured with the phantom according to FIG. 1 in spiral mode with an X-ray computed tomography apparatus of the type SOMATOM PLUS 4 of Siemens AG, wherein the X-ray attenuation coefficient in Hounsfield units is entered versus the table position in mm. The slice sensitivity profiles referenced with "slim" and "wide" differ on the basis of the slice interpolation algorithm employed in their determination. Whereas a linear interpolation over 360° is undertaken for "wide", a linear interpolation over only 180° ensues for "slim".

In the measurement according to FIG. 3, the slice thickness amounted to 1 mm, the table feed per full revolution of the table amounted to 1 mm and the pitch thus amounted to 1. The corresponding values for the measurement according to FIG. 4 are slice thickness 10 mm, table feed 10 mm and pitch 1.

Even for the smallest slice thicknesses of 0.5 mm known in X-ray computed tomography, the phantom according to FIG. 1 meets the demand for a slight axial expanse in z-direction compared to the slice thickness, namely a maximum of $\frac{1}{10}$ of the slice thickness, and still yields a signal of 200 through 300 Hounsfield units given a slice thickness of 10 mm. This signal thus lies above the usual noise values by a factor of approximately 100 and is thus more than adequate for a dependable measurement of the slice profile. The slight diameter of the foil allows a simple positioning of the phantom such that the foil extends parallel to the image plane BE.

Although modifications and changes may be suggested by those skilled in the art, it is the intention of the inventors to embody within the patent warranted hereon all changes and modifications as reasonably and properly come within the scope of their contribution to the art.

We claim:

1. A phantom for measuring slice thicknesses, slice sensitivity profiles and an axial modulation transfer function in an x-ray computed tomography apparatus having an image plane, said phantom comprising a foil of a material that highly attenuates x-rays and which is adapted to be disposed parallel to said image plane when employed in said x-ray computed tomography apparatus, said foil having an axial expanse that is small compared to a thinnest slice to be measured in said x-ray computed tomography apparatus.

2. A phantom as claimed in claim 1 wherein said material has an atomic number of at least 13.

3. A phantom as claimed in claim 2 wherein said material is selected from the group consisting of lead, tantalum and gold.

4. A phantom as claimed in claim 2 wherein said material is composed of at least one material in the group consisting of lead, tantalum and gold.

5. A phantom as claimed in claim 1 wherein said foil has an expanse in said image plane of a few millimeters.

6. A phantom as claimed in claim 1 wherein said foil has a substantially circular contour in a direction perpendicular to said image plane.

7. A phantom as claimed in claim 1 further comprising a homogenous material containing said foil.

8. A phantom as claimed in claim 7 wherein said homogenous material consists of water.

9. A phantom as claimed in claim 7 wherein said homogenous material is a polymeric material.

10. A phantom as claimed in claim 1 further comprising a plurality of additional foils disposed successively in said axial direction.

11. A method for measuring slice thicknesses, sensitivity profiles and an axial modulation transfer function in an x-ray computed tomography apparatus, said method comprising the steps of:

identifying a thinnest slice to be measured in an x-ray computed tomography apparatus having an image plane;

disposing a foil parallel to said image plane composed of a material that highly attenuates x-rays and which has an axial expanse significantly less than said thinnest slice to be measured; and measuring slice thicknesses, slice sensitivity profiles and an axial modulation transfer function in said x-ray computed tomography apparatus using said foil.

12. A method as claimed in claim 11 comprising employing a material having an atomic number of at least 13 as said material for said foil.

13. A method as claimed in claim 11 comprising selecting said material of said foil from the group consisting of lead, tantalum and gold.

14. A method as claimed in claim 11 comprising employing at least one material from the group consisting of lead, tantalum and gold as said material of said foil.

15. A method as claimed in claim 11 comprising embedding said foil in homogenous material.

16. A method as claimed in claim 15 comprising selecting said homogenous material from the group consisting of water and polymeric material.

17. A method as claimed in claim 11 comprising providing a plurality of additional foils, identical to said foil, parallel to said image plane successively in an axial direction in said computed tomography apparatus, and measuring said slice thickness, said sensitivity profiles and said axial modulation transfer function in said x-ray computed tomography apparatus using said foil and said plurality of additional foils.

* * * * *